United States Patent [19]

Lindsey

[11] Patent Number: 4,706,463

[45] Date of Patent: Nov. 17, 1987

[54] RECOVERY OF MICROORGANISM HAVING ICE NUCLEATING ACTIVITY

[75] Inventor: Carole B. Lindsey, Rochester, N.Y.

[73] Assignee: Eastman Kodak Company, Rochester, N.Y.

[21] Appl. No.: 910,552

[22] Filed: Sep. 23, 1986

[51] Int. Cl.[4] ............................................. F25D 17/02
[52] U.S. Cl. .............................................. 62/64; 34/5; 435/260; 435/874
[58] Field of Search .................. 62/78, 64, 100; 34/5, 34/15, 92; 47/2; 435/874, 260, 261

[56] References Cited

U.S. PATENT DOCUMENTS

| | | | |
|---|---|---|---|
| 3,228,838 | 1/1966 | Rinfret et al. | 167/74 |
| 3,928,566 | 12/1975 | Briggs et al. | 62/74 |
| 4,200,228 | 4/1980 | Woerpel | 239/25 |
| 4,235,966 | 11/1980 | Jarman et al. | 435/874 X |
| 4,277,462 | 7/1981 | Strobel | 435/874 X |
| 4,342,746 | 8/1982 | Strobel | 435/874 X |
| 4,377,571 | 3/1983 | Strobel | 435/874 X |
| 4,432,160 | 2/1984 | Lindow | 47/2 |
| 4,479,363 | 10/1984 | Gibson et al. | 62/63 |

OTHER PUBLICATIONS

Vali, "Quantitative Evaluation of Experimental Results on the Heterogenous Freezing of Supercooled Liquids," J. Atoms Sci., vol. 28, 402–409 (1971).
Maki & Willoughby, Bacteria as Biogenic Sources of Freezing Nuclei, J. Applied Meteorology 17 1049–1053.
Koxloff Schofield and Lute, Ice Nucleating Activity of Pseudomonas Syringae and Erwinia Herbicola, J. Bacter 153, pp. 222–231 (1983).

Primary Examiner—Albert J. Makay
Assistant Examiner—Steven E. Warner
Attorney, Agent, or Firm—J. Jeffrey Hawley

[57] ABSTRACT

There is disclosed a method for recovery of a microorganism having ice nucleating activity from a fermentation medium which comprises the steps of (a) bringing the temperature of the medium to a temperature of about 15° C. or less, (b) forming a concentrate of the medium while maintaining the temperature of about 15° C. or less, (c) running the concentrate into a cryogenic fluid to form frozen pellets of the concentrate and (d) freeze drying said pellets at a temperature below 25° C.

5 Claims, No Drawings

RECOVERY OF MICROORGANISM HAVING ICE NUCLEATING ACTIVITY

FIELD OF THE INVENTION

The present invention relates to a method for the recovery, in dried form, of microorganisms that have ice nucleating activity from a medium containing the microorganism.

DESCRIPTION RELATIVE TO THE PRIOR ART

In U.S. Pat. No. 4,200,228 there is disclosed a method for the making of snow whereby microorganisms are included in droplets that are sprayed into the air. The microorganisms that are used are of the type which are known to promote ice nucleation. As a result, snow can be made at temperatures that are much higher than are ordinarily possible. A typical microorganism that is useful in this process is a Pseudomonad and particularly *Pseudomonas syringae.*

It is apparent that if this process is to be used on any scale, large amounts of microorganisms are needed. Further, it is desirable that the microorganism be obtained in a dry form so as to facilitate the storage handling and transport of the material.

The growth conditions for microorganisms that have ice nucleating activity are known in the art. For example, in Maki and Willoughby, Bacteria as Biogenic Sources of Freezing Nuclei, J. Applied Metrorology 17 1049-1053 it is disclosed that the microorganisms such as *Pseudomonas syringae* are grown in Koser citrate broth at a temperature below 20° C., i. e. 5° C. This medium is well known and has a pH of about 6.7. No control of the pH is disclosed in this reference. It is also stated that if the cultures are grown at a temperature above 20° C., very few freezing nuclei are produced.

As far as the recovery process is concerned, this reference discloses that concentrated cultures that had been treated with formalin were freeze dried. No details are given.

In another reference, the microorganisms are grown on a tryptone-yeast extract-glycerol medium which would have a pH of about 7.0. (Koxloff, Schofield and Lute, Ice Nucleating Activity of Pseudomonas syringae and Erwinia herbicola, J. Bacter. 153 pages 222-231 (1983)) In this reference, the microorganisms are not recovered in dry form and the suspensions are tested directly for activity. It is noted that the ice nucleating activity is not stable in the suspension and decreases overnight.

If the known procedures are used for the production of large volumes of the microorganisms, less than the desired ice nucleating activity is obtained. Even where the fermentation produces a high activity in the fermentation suspension, much of the activity is lost during the drying of large volumes of the material. The end result is a process that is not capable of producing commercial quantities of microorganism at reasonable cost. It is to the solution of this problem that the present invention is directed.

SUMMARY OF THE INVENTION

The present invention provides a method for the recovery of a microorganism which has ice nucleating activity from a fermentation medium. The method comprises the steps of:

(a) bringing the temperature of said medium to a temperature of about 15° C. or less,
(b) forming a concentrate of said microorganism preferably having a water content of about 15-27%, while maintaining the temperature of about 15° C. or less,
(c) running said concentrate into a cryogenic liquid in the form of a fine stream so as to form frozen pellets of the concentrate preferably having a diameter of about 2-10 mm,
(d) freeze drying said pellets at a temperature below 25° C.

DETAILED DESCRIPTION OF THE INVENTION

The process of the present invention is capable of preserving the ice nucleating activity (INA) after drying of any suspension containing the microorganisms. As noted above, fermentation processes for these microorganisms are well known in the art.

A particularly preferred process is described in copending, commonly assigned U.S. patent application Ser. No. 910,600, filed of even date herewith entitled "Fermentation of Microorganisms having Ice Nucleating Activity" of Hendricks, Ward and Orrego.

Any microorganism that has ice nucleation activity can be recovered by the present invention. Suitable microorganisms include Pseudomonads such as *P. syringae* and *P. fluorscens, P. coronafaciens* and *P. pisi.* Other microorganisms that are useful in the present invention include *Erwina herbicola.* The presently preferred microorganism is *P. syringae* ATCC No. 53,543 deposited on Sept. 23, 1986 in accordance with the Budapest Treaty with the American Type Culture Collection in Rockville, Md., USA.

I have found that the present method for the recovery of the microorganisms results in less loss of the INA than known methods. In the process of the present invention, it is important to keep the temperature of the microorganisms as low as is practical during the process. The presently preferred process is to first reduce the temperature of the fermentation medium to a temperature below 15° C. The medium is then concentrated to a dry solid by weight concentration of preferably between 15 and 27% and more preferably 22% while keeping the temperature below 15° C. This concentrated medium is then rapidly frozen in a cryogenic liquid such as liquid nitrogen.

Concentration of the medium can be by any conventional method such as filtration or centrifugation. A solid bowl centrifuge or a disc bowl continuous centrifuge can be used.

The concentrated medium is run into the cryogenic liquid in the form of a continuous stream of the medium. When the stream meets the liquid, small droplets form and rapidly freeze into pellets preferably having a size of about 2-10 mm.

Apparatus and methods for introducing liquids similar to the concentrated fermentation medium into the cryogenic liquid are known in the art. Reference is made to U.S. Pat. Nos. 3,228,838; 3,928,566; 4,077,227; and 4,479,363.

The pellets are then recovered from the cryogenic liquid and freeze dried by conventional methods, preferably to a moisture content of about 2-8% by weight. During the freeze drying process, the product temperature is preferably maintained at a temperature of 25° C. or less, and preferably 15° C. or less, in order to retain as much of the INA as is possible. We have found that higher product temperature results in some INA loss. Product temperatures of from 30° to 50° C., for example, can cause a 30-70% loss of INA.

In the examples presented below, the INA is calculated using conventional techniques. The INA is determined by placing a plurality of microorganism containing water droplets (10 μl) on paraffin coated aluminum foil. The foil is maintained at −5° C. by placing it on a constant temperature bath. Details regarding this procedure are found in the literature, for example, Vali, Quantitative Evaluation of Experimental Results on the Heterogenous Freezing of Sypercooled Liquids, J. Atoms Sci., 28, 402-409 (1971). The INA reported in the examples is the number of ice nucleating sites per dry gram of microorganism. For the present purposes, the INA which is measured using a sample directly from the fermentor without drying will be referred to as "Fermentor INA" and the INA of the recovered dried product will be referred to as the "Recovered INA".

The following examples are submitted for a further understanding of the invention.

EXAMPLE 1

*Pseudomonas syringae* ATCC 53,543 was streaked on an agar plate containing a nutrient medium containing mannitol, yeast extract and magnesium sulfate. After 48 hours at 26° C., five plates were used to innoculate a 10 liter fermentor also containing a similar medium.

After 12 hours at 26° C. this liquid seed was used to innoculate 100 L liters of a fermentation medium. The medium was as described in Table I of U.S. Ser. No. 910,600 except that it also contained 0.1 g/l of the vegetable based antifoaming agent Struktol ®.

The fermentation temperature was controlled at 21° C. During the fermentation, the pH was controlled with 4N sulfuric acid and 2N sodium hydroxide. The acid was added when the pH approached 6.6 and the base was added when the pH approached 5.6. The dissolved oxygen was maintained at greater than 30% saturation. The antifoaming agent was added as needed to control foaming.

After 24 hours, the cell mass reached 18 g dry cells/liter. The Fermentor INA was $3.70 \times 10^{11}$.

The fermentation broth was cooled to a temperature of 5° C. and centrifuged while the temperature was maintained at 5° C. The solids were collected and slurried to a solids content of 22%. The slurry was run into a container filled with liquid nitrogen. The diameter of the stream that was run into the nitrogen was about 1-4 mm. The pellets that were thus formed were collected and freeze dried. During the freeze drying process, the product temperature was not allowed to exceed 21° C. The Recovered INA of the dried material was $1.26 \times 10^{11}$.

EXAMPLE 2

This is a comparative example.

Example 1 was repeated except that the product temperature during the freeze drying step was about 35° C. The Recovered INA was $0.25 \times 10^{11}$.

EXAMPLE 3

This is a comparative example.

Example 1 was repeated except that the fermentation medium was maintained at a temperature of 21° C. after the fermentation and for a period of 4 hours of room temperature (25° C.) before the concentration and pelletizing steps. The Recovered INA was $0.36 \times 10^{11}$.

EXAMPLE 4

This is a comparative example.

The fermentation medium in Example 1 was poured into shallow pans to a depth of about 2.54 cM. The pans were then placed into a freezer (−6° C.) until the medium was completely frozen thereby forming a slab of the frozen medium. The pans were then placed into a freeze dryer wherein the product temperature was kept below 21° C. The resulting dried product had a Recovered INA of $0.40 \times 10^{11}$.

TABLE

Example Summary

| Example | Medium Form | Freeze Dry Temperature | Recovered INA × $10^{-11}$ |
|---|---|---|---|
| 1 | pellets | <25° C. | 1.26 |
| 2 (C) | pellets | 35° C. | 0.25 |
| 3 (C) | warm | <25° C. | 0.36 |
| 4 (C) | slab | <25° C. | 0.40 |

The invention has been described in detail with particular reference to preferred embodiments thereof, but it will be understood that variations and modifications can be effected within the spirit and scope of the invention.

What is claimed is:

1. A method for the recovery of a microorganism which has ice nucleating activity from a fermentation medium said method comprising the steps of:
   (a) bringing the temperature of said medium to a temperature of about 15° C. or less,
   (b) forming a concentrate of said microorganism while maintaining the temperature of about 15° C. or less,
   (c) running said concentrate into a cryogenic liquid in the form of a fine stream so as to form frozen pellets of the concentrate, and
   (d) freeze drying said pellets at a temperature below 25° C.

2. A method according to claim 1 wherein said solids by weight concentration in step (b) is between about 15 and 27%.

3. A method according to claim 1 wherein the product temperature in freeze drying step (d) is maintained below 15° C.

4. The method according to claim 1 wherein said microorganism is a Pseudomonad.

5. The method according to claim 2 wherein said microorganism is *P. syrinage.*

* * * * *